United States Patent [19]

Haralambidis et al.

[11] Patent Number: 5,525,465
[45] Date of Patent: Jun. 11, 1996

[54] OLIGONUCLEOTIDE-POLYAMIDE CONJUGATES AND METHODS OF PRODUCTION AND APPLICATIONS OF THE SAME

[75] Inventors: Jim Haralambidis, Box Hill South; Geoffrey W. Tregear, Hawthorn, both of Australia

[73] Assignee: Howard Florey Institute of Experimental Physiology and Medicine, Parkville, Australia

[21] Appl. No.: 367,904

[22] Filed: Jan. 3, 1995

Related U.S. Application Data

[63] Continuation of Ser. No. 162,789, Dec. 6, 1993, abandoned, which is a continuation of Ser. No. 477,995, Jul. 16, 1990, abandoned.

[30] Foreign Application Priority Data

Oct. 28, 1987 [AU] Australia .............................. PI5111/87

[51] Int. Cl.$^6$ .............................. C12Q 1/68; C07H 19/10; G01N 33/50
[52] U.S. Cl. .............................. 435/6; 435/810; 436/501; 536/22.1; 536/23.1; 536/24.1; 536/24.3; 536/24.31; 536/24.32; 536/24.33; 536/25.3; 935/77; 935/78; 935/88
[58] Field of Search .......................... 435/6, 810; 436/501; 536/27.1, 23.1, 24.1, 24.3–.33, 25.3; 935/77, 78, 88

[56] References Cited

U.S. PATENT DOCUMENTS 4,828,979  5/1989  Klevan et al. .............................. 435/6

FOREIGN PATENT DOCUMENTS

16179/83  1/1984  Australia .
46484/85  3/1986  Australia .
154884  9/1985  European Pat. Off. .
187332  7/1986  European Pat. Off. .

OTHER PUBLICATIONS

Lehninger, *Biochemistry*, "Molecular Basis of Cell Structure and Function", 2d Ed., pp. 932–936, Worth Publishers, Inc. (1978).

Chu, B. C. F. et al., "Derivation of unprotected polynucleotide" Nucleic Acids Research, 11 (18), issued 1983 (IRL Press Ltd., Oxford, England) pp. 6513–6529.

*Biochemistry* (1970) A. L. Lehninger (Worth Publishers, New York, NY) p. 695.

*Primary Examiner*—W. Gary Jones
*Assistant Examiner*—Ardin H. Marschel
*Attorney, Agent, or Firm*—Walter H. Dreger; Jan P. Brunelle

[57] ABSTRACT

Oligonucleotide-polyamide conjugates of the formula X—L—Y, where X is a polyamide, Y is an oligonucleotide, and L is a linker which forms a covalent bond with the amino-terminus of the polyamide X and the 3' phosphate group of the oligonucleotide Y. Conjugates may be synthesized by assembling a polyamide on a solid support matrix, adding a suitable linker molecule, followed by synthesis of the oligonucleotide. Methods for detecting specific polynucleotides with oligonucleotide-polyamide conjugates are also described.

19 Claims, 5 Drawing Sheets

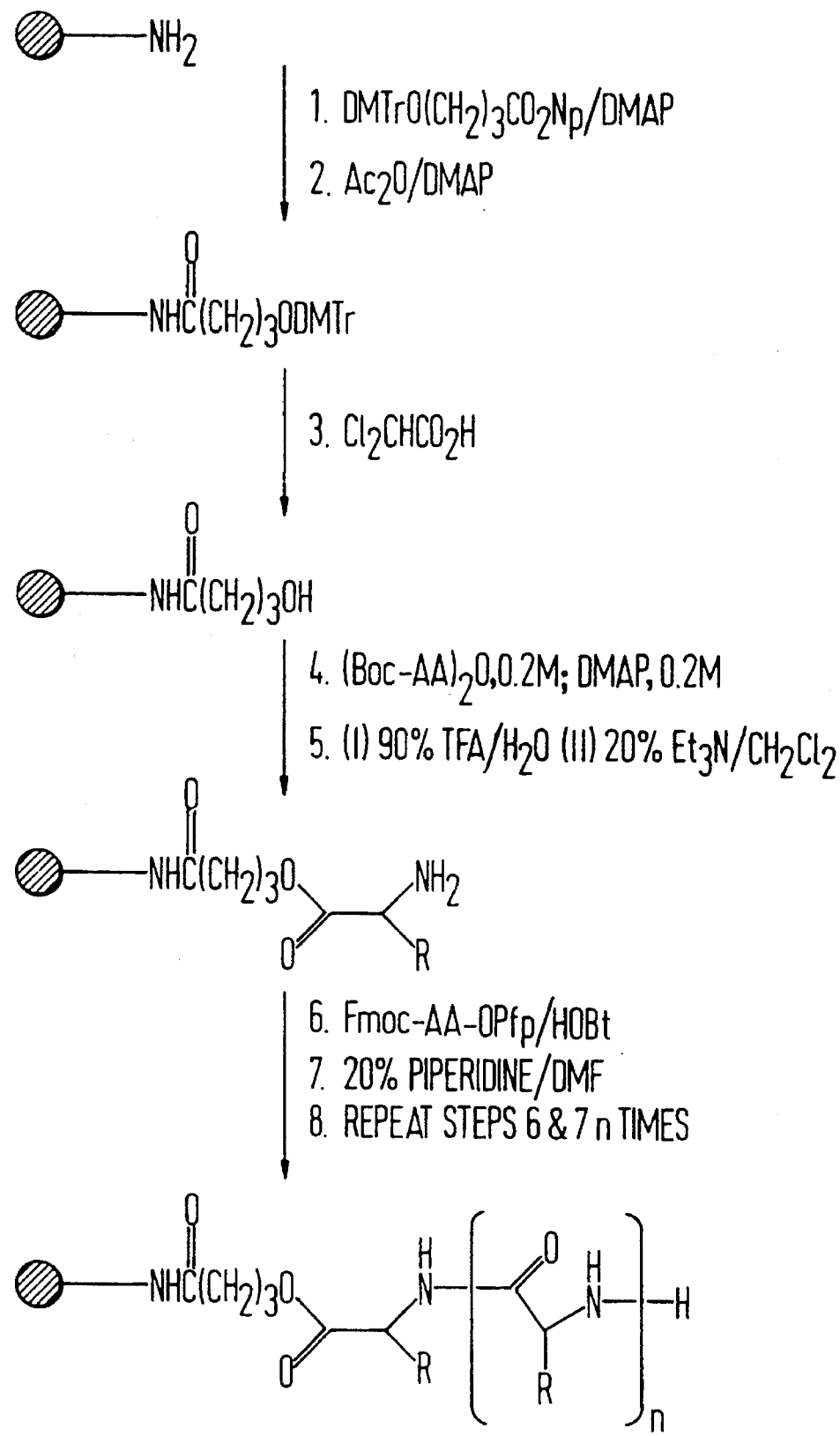
FIG._1

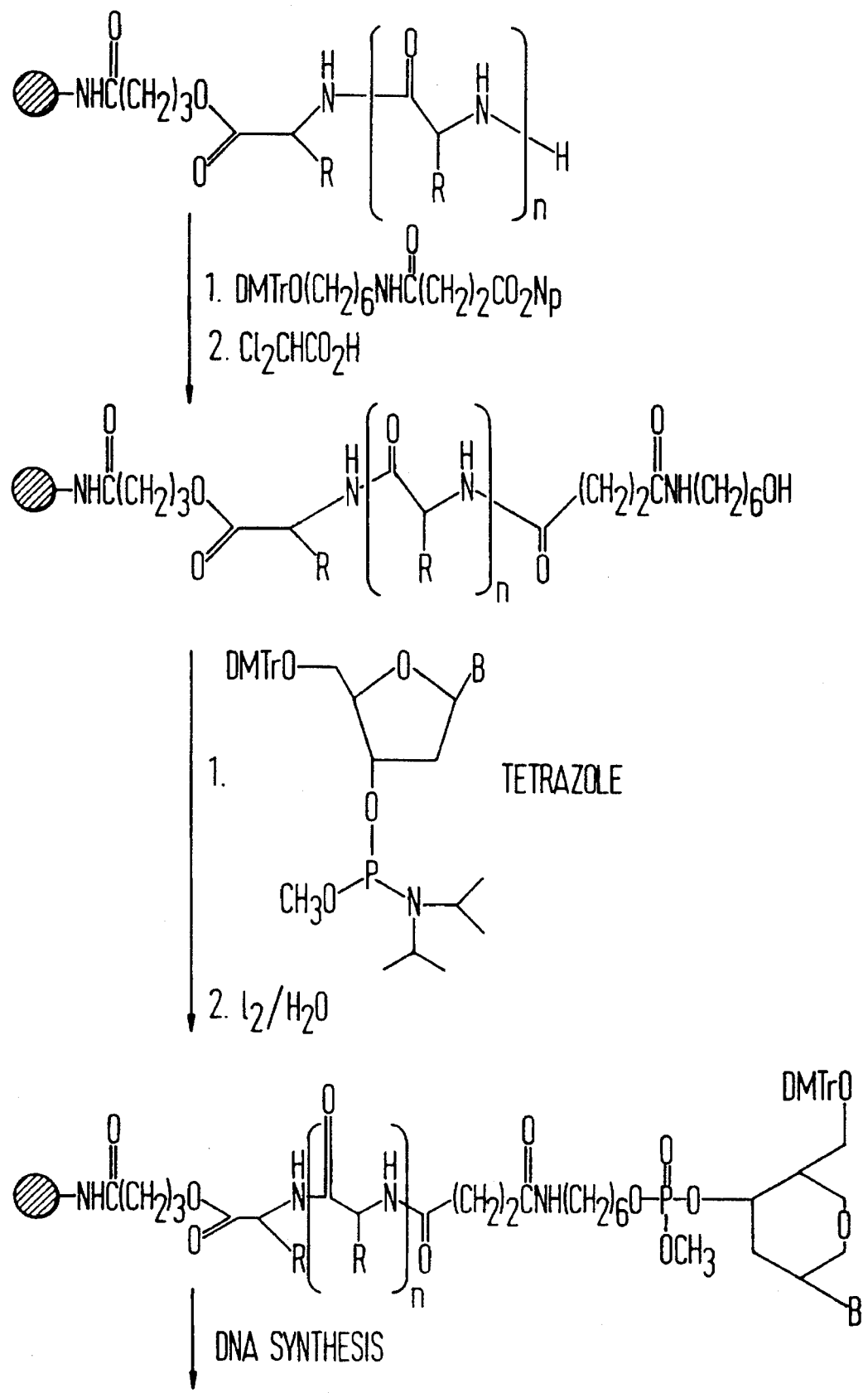
FIG._2

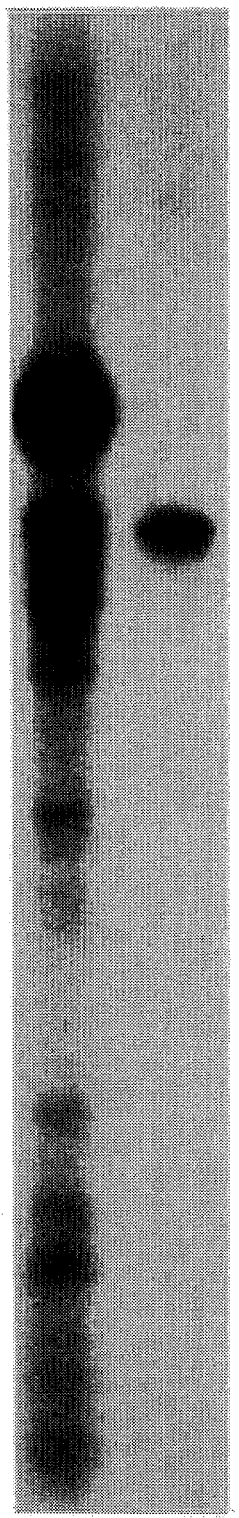
FIG._3

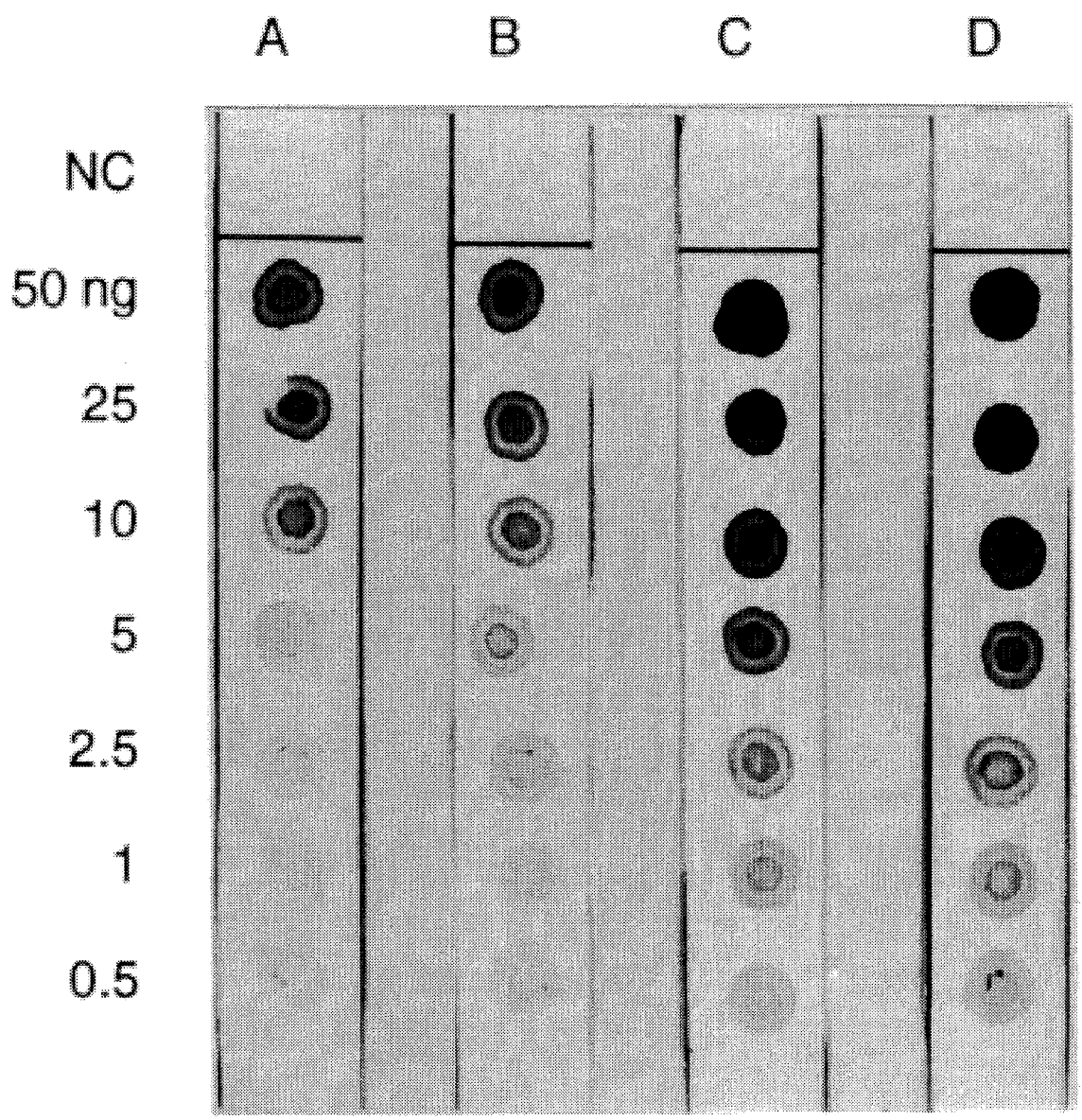
FIG._4

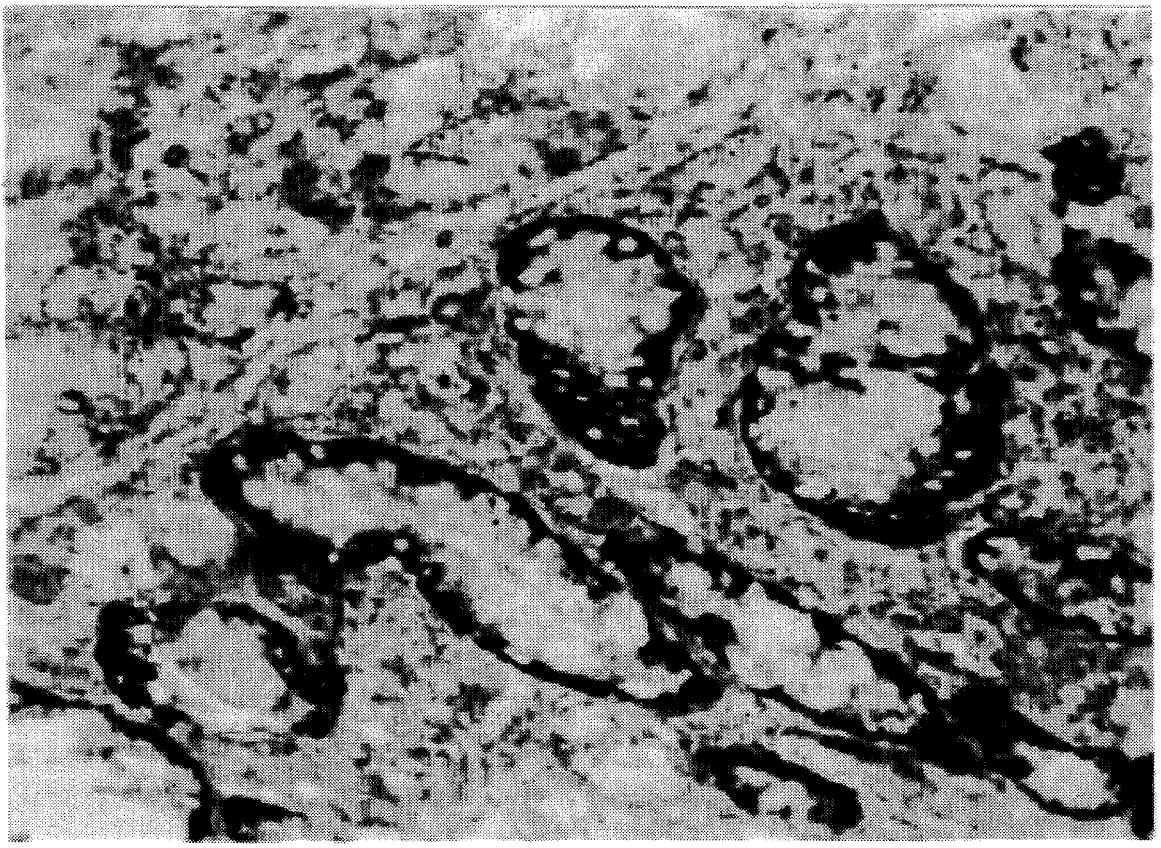
FIG._5

OLIGONUCLEOTIDE-POLYAMIDE CONJUGATES AND METHODS OF PRODUCTION AND APPLICATIONS OF THE SAME

This is a continuation of application Ser. No. 08/162,789, filed 6 Dec. 1993, now abandoned, which is a continuation of Ser. No. 07/477,995; filed 16 Jul. 1990, now abandoned.

The present invention relates to oligonucleotide-polyamide conjugates, their methods of production, and the uses of such conjugates, particularly as diagnostic and therapeutic reagents.

Synthetic oligonucleotides have found wide application in the field of molecular biology, particularly as hybridization probes for the detection of DNA or RNA sequences. Generally, the oligonucleotide carries a radiolabel at its 5' end to enable detection of hybridization. Apart from the problems normally associated with radiolabelled materials such as cellular toxicity and mutagenicity, the detection of radiolabelled probes requires autoradiographic exposure, often for several days. Additionally, radiolabels may have a short half-life, thereby limiting their capacity for storage and subsequent use.

The labelling of oligonucleotides with non-radioactive probes or reporter groups such as fluorescent or enzymic reporter groups, offers significant advantages over radiolabelled probes, including greater safety, indefinite shelf life and ease of detection.

It has been proposed to label oligonucleotides with non-radioactive reporter groups through one or more nucleotide bases (U.S. Pat. No. 4,669,876 and published Australian Patent Application No. 16484/85) or by directly coupling a reporter group to the 3' or 5' ends of an oligonucleotide (published European Patent Application Nos. 84101392.3 and 85102130.3). Such prior proposals often involve complex synthetic reactions and may disrupt the hybridization of the oligonucleotide to a complementary target sequence.

A requirement accordingly exists for oligonucleotides which hybridize efficiently to complementary target sequences and which can be conveniently detected without recourse to radioactive labels, and further, which can be relatively simply and conveniently prepared.

According to the present invention there is provided an oligonucleotide-polyamide conjugate of the formula X—L—Y, where X is a polyamide, Y is an oligonucleotide, and L is a linker which forms a covalent bond with the amino-terminus of the polyamide X and the 3' phosphate group of the oligonucleotide Y.

The polyamide may be formed from naturally occurring amino acids (Biochemistry, 2nd Edition, Albert L. Lehninger, pp. 72–77 (1970)), such as lysine, valine, glycine, serine, threonine, tyrosine, methionine, proline, etc. linked through amide or so-called peptide bonds. Alternatively, the polyamide may be formed from synthetic amino acids (that is, amino acids which do not occur naturally in proteins) or a combination of natural and synthetic amino acids. The term "synthetic amino acids" used herein refers to α,ω-amino carboxylic acids which may be represented by the general formula $H_2NCHRCOOH$, where R is any organic moiety such as alkyl or cycloalkyl which may unsaturated or partly saturated and/or interrupted by one or more hereto atoms or groups containing such hetero atoms such as amide groups and/or substituted with halogen, cyano, amino or unsubstituted or substituted phenyl or benzyl.

The polyamide may contain any number of amino acid units, with the proviso of course that it does not interfere with the hybridization of the oligonucleotide with its target sequence. By way of example only, the polyamide may contain from 1 to 100 amino acid units.

The polyamide may form a peptide comprising naturally occurring α-amino acids. The sequence of the peptide can be designed to suit any desired application of the oligonucleotide-polyamide conjugate. The peptide may contain one or more lysine residues which can be derivatized with a reporter group as will be hereinafter described. Furthermore, the polyamide may be antigenic, and thus detectable by the binding of antibodies, which may, for example, contain suitable reporter groups to allow detection of antibody binding.

Synthetic amino acids may, for example, be used as spacers between amino acids such as lysine, which carry reporter groups, so as to avoid quenching or steric inhibition of reporter groups, or to distance a bulky reporter group from the oligonucleotide. An example of a useful amino acid spacer is 6-aminohexanoic acid (Aha).

Synthetic amino acids which may be employed in the invention include compounds of the formula:

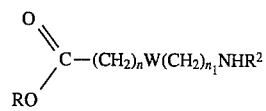

where:

RO is a leaving group such as p-nitrophenyloxy, pentafluorophenyloxy and N'-hydroxysuccinimidyl; or R is hydrogen;

$R^2$ is an amino protecting group such as fluorenylmethoxycarbonyl (Fmoc) or tert-butoxycarbonyl (Boc);

n and $n_1$ are the same or different and represent an integer from 1 to 30;

W is

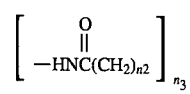

where $n_2$ and $n_3$ are the same or different and represent an integer from 0 to 100, wherein if $n_3$ is 0, then n and $n_1$ are not both 0;

An amino acid unit useful in polyamide synthesis is

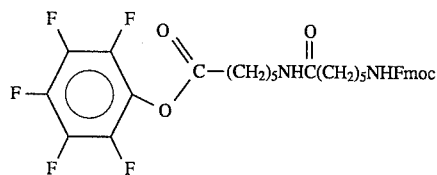

It is to be understood that the synthetic amino acids which may be used to form the polyamide are in no way restricted to the compound specifically exemplified above.

The polyamide X may be labelled with one or more reporter groups (also referred to as detectable markers) such as biotin, fluorophores, chemiluminescent moieties, enzymes or colloidal compounds such as ferritin or colloidal silver or gold.

Fluoro phore reporter groups may be selected from:

fluore scein-5-isothiocyanate, diacyl (such as isobutyryl, acetyl or pivaloyl) fluorescein-5 and/or 6 carboxylic acid pentafluorophenyl ester, 6-(diacyl- 5 and/or 6-carboxamidofluorescein)aminohexanoic acid pentafluorophenyl ester, Texas Red (Trademark of Molecular Probes, Inc.) tetramethylrhodamine-5 (and -6) isothiocyanate, eosin-isothiocyanate, erythrosin- 5-isothiocyanate, 4-chloro-7-nitrobenz-2-oxa-1,3-diazole, 4-fluoro-7-nitrobenz-2-oxa-1,3-diazole, 3-(7-nitrobenz-2-oxa-1,3-diazol-4-yl) methylaminopropionitrile, 6-(7-nitrobenz-2-oxa-1,3-diazol-4-yl)aminohexanoic acid, succinimidyl 12-(N-methyl-N-(7-nitrobenz-2-oxa-1,3-diazol-4-yl)aminododecanoate, 7-diethylamino-3-(4'-isothiocyanatophenyl)-4-methylcoumarin (CP), 7-hydroxycoumarin-4-acetic acid, 7-dimethylaminocoumarin-4-acetic acid, succinimidyl 7-dimethylaminocoumarin-4-acetate, 7-methoxy-coumarin-4-acetic acid, 4-acetamido-4'-isothiocyanatostilbene-2-2'-disulfonic acid (SITS), 9-chloroacridine, succinimidyl 3-(9-carbazole)propionate, succinimidyl 1-pyrenebutyrate, succinimidyl 1-pyrenenpnanoate, p-nitrophenyl 1-pyrenebutyrate, 9-anthracenepropionic acid, succinimidyl anthracene-9-propionate, 2-anthracenesulfonyl chloride; or fluorophore precursors, which when treated in a particular manner fluoresce.

Enzymic reporter groups may be selected from β-galactosidase, horseradish peroxidase, urease, alkaline phosphatase, dehydrogenases, luciferase and carbonic anhydrase. Generally, enzymes will react with one or more substrates to produce a detectable signal such as a color change, luminescence or formation of a precipitate.

Reporter groups may be attached to polyamides according to conventional techniques known per se in the art. For example, nucleophilic groups on polyamides such as primary amine groups may react with the fluorescent or enzymic reporter groups to form a covalent bond therebetween. Alternatively, bifunctional coupling reagents known per se in the art (for example as described in the Pierce Chemical Company catalogue, 1987) may be employed to attach reporter groups to polyamides.

Biotinylated oligonucleotides may be prepared by conventional methods. For example, underivatised biotin may be incorporated into an oligonucleotide utilizing BOP coupling methodology (Castro, B. et al., Synthesis (1976), pp. 751–752). Alternatively, biotin can be introduced as the N-hydroxysuccinimidyl active ester. Biotin may be detected using avidin attached to a reporter group. For example, a streptavidin-alkaline phosphatase conjugate may be employed to bind to biotin. The alkaline phosphatase can react with a suitable substrate to generate an insoluble dye precipitate which can be detected visually.

Where it is desired to detect the polyamide by way of immunological reaction, antibodies directed against the polyamide may be raised in suitable host animals by immunization with oligonucleotidepolyamide conjugates, the polyamide alone, or the polyamide associated with a carrier molecule, for example, KLH (key hole limpet haemocyanin), according to methods well known in the art (for example, Goding, J. W. (1986), Monoclonal Antibodies: Principles and Practice, 2nd Edition, Academic Press).

The oligonucleotide may be of any desired sequence which allows hybridization to a complementary nucleotide sequence in a DNA or RNA target. The number of nucleotides which constitutes the oligonucleotide is generally unimportant, as long as sufficient nucleotides are present to allow hybridization to a target sequence. Usually, the oligonucleotide will contain in excess of six nucleotides. The oligonucleotide may be suitably modified to increase its half-life in-vivo without effecting hybridization. For example, the oligonucleotide may be modified by replacing one or two of the non-bridging oxygens on the phosphorous backbone with sulphur or amines, according to the procedures of Argawal et al. (1988, Proc. Natl. Acad. Sci. USA 85, pp. 7079–7083) or Stein and Cohen, (1988, Cancer. Res. 48, pp. 2659–2688). Such modified oligonucleotides are within the scope of the term oligonucleotide. The term "oligonucleotide" may also include a single nucleotide.

The linker L refers to a moiety derived from a bifunctional molecule R'—L'—R", wherein R' and R" are the same or different and represent such functional groups as —$NH_2$, —$CO_2H$, —OH, OR where R is a hydroxy protecting group, —$CO_2R$, where R is 2-hydroxypyridine, N-hydroxysuccinimide, p-nitrophenyl, pentafluorophenyl (Pfp), Me or other active esters, acylimidazole, maleimide, trifluoroacetate, diketone, imidoesters, sulfonate esters, imine, —CHO, 1,2-cyclohexanedione, glyoxal, sulfonyl halides, alpha halo ketones, azide, etc, and L' is an alkyl or substituted alkyl group. Alkyl chain L' can be substituted with such common substituents as halogen, (I, Br, Cl, F), hydroxy, cyano, phenyl, amino, carboxy, alkyl, alkoxy and others. Further, the alkylene chain of linker L' can be interrupted by one or more bivalent groups, such as —O—, —S—, —NH— —CH=CH—, —C=C—, phenyl, —$SO_2$—, etc. However, functional group R' must be capable of forming under appropriate conditions, a covalent bond with the amino terminus of a polyamide and functional group R" must be capable of forming, under appropriate conditions, a covalent bond with a nucleotide. Clearly the choice of linking group R'—L—R" and a particular conjugation chemistry must reflect the need to preserve other macromolecular bonds critical to the integrity of the resulting probe molecule, i.e. peptide, glycosidic and phosphodiester bonds.

The linker may be derived from an α,ω hydroxy carboxylic acid derivative.

Alternatively the linker L may be a bond, or a lactone such as butyrolactone.

The present invention also provides a method for the production of an oligonucleotide-polyamide conjugate comprising the step of linking the 3'-terminal end of an oligonucleotide to the amino terminus of a polyamide.

Thus, in accordance with one aspect of the method, the conjugate may be produced by attaching a linking group to either a preformed oligonucleotide moiety or a preformed polyamide moiety and then attaching the remaining moiety to the linking group.

Alternatively, appropriate linking group precursors may be attached to the preformed oligonucleotide moiety and the preformed polyamide moiety. Reaction of the two precursors then results in the formation of the linking group.

In accordance with a further aspect, the method comprises attaching the linking group to a preformed polyamide and thereafter attaching a nucleotide base to the linking group and then sequentially adding one or more further nucleotide bases to form an oligonucleotide.

In a still further aspect, the method comprises attaching the linking group to a preformed oligonucleotide and thereafter attaching an amino acid to the linking group and then sequentially adding one or more amino acids to form a polyamide.

The polyamide moiety may be connected to a solid support matrix such as controlled pore glass (CPG).

In accordance with a particularly preferred aspect of the present invention, there is provided a method for the production of an oligonucleotide-polyamide conjugate, said method comprising the steps of:

(a) reacting the C-terminus of a first amino acid or a unit of amino acids (linked together by amide bonds) with a support matrix to form a bond therebetween;

(b) thereafter sequentially reacting the support matrix with one or more amino acids, according to well-known solid-phase peptide synthetic techniques to form a polyamide;

(c) reacting the support matrix-polyamide with a first reactive group of a linker to form a bond between the amino terminus of the polyamide and the linker;

(d) reacting the product of step (c) with a first nucleotide to form a bond between a second reactive group on the linker and the 3' phosphate of the nucleotide;

(e) thereafter sequentially reacting the support matrix with one or more nucleotides, according to well-known solid phase oligonucleotide synthetic methods to form an oligonucleotide; and (f) optionally cleaving the oligonucleotide-polyamide conjugate from the support matrix and removing any protecting groups associated with reactive groups of the polyamide or oligonucleotide, and purifying the resulting conjugate.

When the linker L is a bond, step (c) is omitted.

Polyamides may, for example, be synthesized using solid phase Fmoc (Atherton, R. and Shepard, R. C. (1985) J. Chem. Soc. Commun, pp. 165–166) or solid phase Boc (Barany, G. and Merrifield, R. B. (1980) Solid-Phase Peptide Synthesis in "The Peptides", Vol. 2, E. Gross & J. Meienhofer Eds., Academic Press, New York, pp. 1–284) methodologies. In these methods, the amino acids are protected with standard protecting groups known per se in the art (for example, Green (1981) Protective Groups in Organic Synthesis, John Wiley & Sons, Inc.; Atherton and Sheppard (1985) J. them. Soc. Commun, pp. 165–166; Barany and Merrifield, Supra) to protect reactive moieties.

Oligonucleotides may be synthesized by the solid phase phosphotriester method (Sproat and Gait (1984) Oligonucleotide Synthesis, A Practical Approach, pp. 83–116, IRL Press, Oxford), solid phase H-phosphonate method (Froehler et al. (1986) Nucleic Acids Research, 14, pp. 5399–5407) or the solid phase phosphoramidite method (Beaucage and Caruthers (1981) Tetrahedron Lett., 22, pp. 1859–1862). In each of these methodologies, reactive groups such as hydroxy or amino groups may be protected with standard hydroxy and amino protecting groups as described by (Green (1981) Protective Groups in Organic Synthesis, John Wiley & Sons, Inc.; Beaucage, S. L. and Caruthers, M. H. (1981) Tetrahedron Lett., 22, pp. 1859–1862; Sproat, S. and Gait, M. J. (1984) Oligonucleotide Synthesis, A Practical Approach, pp. 83–116, IRL Press, Oxford).

On completion of synthesis of the oligonucleotide-polyamide conjugate, deprotection may be carried out according to methods known per se in the art.

The oligonucleotide-polyamide conjugate of the present invention may be fully protected and attached to a support matrix, protected form detached from the support matrix, or in a fully deprotected form. Each of these states are within the scope of the term "oligonucleotide-polyamide conjugate".

The support matrix may, for example, be selected from controlled pore glass such as aminopropyl controlled pore glass (AP-CPG) or polystyrene resins. The support matrix coupled to the polyamide constitutes a solid support upon which oligonucleotide synthesis takes place.

The preferred method of synthesis of the oligonucleotide-polyamide conjugates of the present invention is advantageous in that large batches of the polyamide connected through its C-terminal to the support matrix may be prepared in advance and aliquots used for the assembly of a desired oligonucleotide when required. Additionally, stepwise synthesis results in excellent yields of the oligonucleotide-polyamide conjugate, which are greater than those achieved by coupling a preformed oligonucleotide to a preformed polyamide.

The polyamide may be synthesized in a standard commercial peptide synthesizer (available, for example, from Applied Biosystems Inc.), and then transferred to a standard commercial oligonucleotide synthesizer (such as supplied by Applied Biosystems Inc.) for synthesis of the oligonucleotide.

One or more reporter groups may be introduced into the polyamide at a number of different stages. The reporter group can be present in the amino acids prior to polyamide synthesis (stage I); it can be introduced after polyamide synthesis (stage Ia); after addition of the linker (stage II); after oligonucleotide synthesis on the support matrix (stage III); or after deprotection and purification of the oligonucleotide-polyamide conjugate from the support matrix (stage IV). The method chosen will depend upon the choice of reporter groups and synthetic procedure.

If the reporter group is stable to the conditions of both peptide and oligonucleotide synthesis, it can be incorporated from the start of polyamide synthesis, as a derivatized amino acid (stage Ia). If it is stable to the conditions of DNA synthesis but not those of peptide synthesis, it can be incorporated after the polyamide has been synthesized (stages I or II). If the reporter group is not stable to either peptide or oligonucleotide chain assembly, but is stable to deprotection methods, it can be incorporated after oligonucleotide chain assembly of the fully protected polyamideoligonucleotide conjugate (stage III). These methods are convenient, since the label is being introduced while the polyamide-oligonucleotide conjugate is still on the solid support, and thus an excess of reporter group can be used and the excess simply washed away after reaction. If the label is not stable to any of the conditions used in the synthesis of the conjugates, it can be introduced in a solution phase reaction with the purified fully deprotected polyamide-oligonucleotide conjugate (stage IV).

Fluorophores may be introduced into the oligonucleotide-polyamide conjugate at any of stages I to IV. This is also the case for biotin.

Enzymes, and colloidal compounds such as colloidal gold, colloidal silver, or ferritin may be introduced at stage IV.

The polyamide portion of the oligonucleotidepolyamide conjugate may contain multiple reporter groups which may increase the detectable signal produced therefore facilitating detection.

The polyamide portion of the conjugate not only functions as a vehicle for attaching a reporter group, but may also act as an address marker to target a polyamide to a particular cell type, cellular location, or enhance the passage of an oligonucleotide through a cellular membrane. The address label activity of peptide sequences is well established (Verner and Schatz (1988) Science 241, pp. 1307–1313; and Goldlath et al. (1986) Nature 322, pp. 641–644). By selecting a peptide sequence which is, for example, recognized by a cell surface receptor, oligonucleotides conjugated to that peptide sequence may be transported into specific cell types where they can exert a biological effect, such as, in the case of anti-sense oligonucleotides, blocking transcription of viral or cellular RNA.

In another aspect of the invention there is provided a method for the treatment of vital, bacterial or other diseases, characterised in that a patient in need of such treatment is administered a therapeutically effective amount of an oligonucleotide-polyamide conjugate of the present invention, and further characterised in that the oligonucleotide portion of the conjugate is an anti-sense oligonucleotide which is complementary to a specific vital, bacterial or other polynucleotide, such that transcription or translation of the specific polynucleotide is blocked.

The hybridization of anti-sense oligonucleotides to specific target polynucleotides may inhibit the synthesis of vital or bacterial proteins associated with vital or bacterial integrity or propagation, and/or the synthesis of toxins.

The reference to "other diseases" pertains to disease states due to expression of genes endogenous to a cell. For example, mRNA encoding a protein causing or contributing to cellular transformation such as the myc protein, may be inactivated with the polyamide-oligonucleotide conjugates of the invention bearing an appropriate anti-sense oligonucleotide.

A therapeutically effective amount of an oligonucleotide is that which blocks transcription or translation of a desired polynucleotide. This amount will vary according to the abundance of the desired polynucleotide and/or its rate of synthesis, the rate of cellular uptake and/or stability of the conjugate, and the weight and age of the subject being treated. In each case, what constitutes a therapeutically effective amount would be based on a determination made by a consulting physician or veterinarian.

The polyamide moiety of the oligonucleotidepolyamide conjugates may also act to stabilise the oligonucleotide moiety from cellular degradation (Le Maitre et al. (1987) Biochemistry 84; pp. 648–652).

Alternatively, the oligonucleotide moiety may enhance the properties of the polyamide, such as, for example, improving its solubility.

According to a yet further aspect of the present invention, there is provided a polyamide intermediate having the formula Z—X—L, where Z represents a solid phase matrix, X represents a polyamide linked through its C-terminus to the solid phase matrix, and L represents a bifunctional linker having a first reactive group which is attached to the N-terminus of the polyamide, and a second reactive group which is capable of forming a bond with the 3' phosphate of a nucleotide.

This polyamide is an intermediate in the synthesis of the conjugates of the present invention. An oligonucleotide may be directly synthesized on the second reactive group of the bifunctional linker L.

The conjugates of the present invention have considerable utility as hybridization probes for the detection of specific DNA or RNA sequences in a target sample. Binding of the oligonucleotides to target sequences is detected by reporter groups attached to the polyamide or by antibodies which bind to the polyamide. The conjugates of the present invention may therefore be used in the detection of vital nucleic acids, such as the AIDS virus or Hepatitis virus, bacterial nucleic acids, or DNA associated with genetic disorders such as muscular dystrophy or cystic fibrosis. The conjugates of the invention may be employed in hybridization to target sequences bound to a matrix such as nitrocellulose, derivatized paper or nylon membranes. Alternatively, the conjugates may be employed in in-situ hybridization (also known as "hybridization histochemistry") to tissue sections to detect target polynucleotides within the tissue section.

In another aspect of the invention there is provided a method for detecting the presence or absence of a specific viral, bacterial or other polynucleotide in a biological sample comprising contacting the nucleic acids of the sample with an oligonucleotide-polyamide conjugate of the present invention wherein the oligonucleotide portion of the conjugate is complementary to a portion of a target polynucleotide, and thereafter detecting whether hybridization of the conjugate has occurred.

A biological sample may comprise a biological fluid such as blood or plasma; cells, such as lymphocytes; or a tissue biopsy. Nucleic acids, that is, DNA or RNA, from the sample may be extracted and detected with the conjugate, according to methods known per se in the art. The conjugate may itself be labelled with reporter groups for detection of hybridization, or alternatively, conjugate bound to a target polynucleotide may be suitably detected, with, for example, antibody reagents.

In a further aspect of the invention there is provided a method for detecting a specific polynucleotide immobilized to or otherwise associated with a support matrix, said method comprising contacting the support matrix with an oligonucleotide-polyamide conjugate according to the present invention, wherein the oligonucleotide portion of the conjugate is complementary to a portion of the target polynucleotide, and thereafter detecting hybridization of the conjugate to the support matrix.

In another aspect of the invention there is provided a method for determining the presence and location in animal or plant tissue of a specific polynucleotide population which comprises:

(a) preparing a section of the tissue to be examined;

(b) hybridizing the tissue section with an oligonucleotide-polyamide conjugate according to the present invention, wherein the oligonucleotide portion of the conjugate is complementary to a portion of a target polynucleotide;

(c) removing unhybridized probe material from the tissue section; and (d) detecting or identifying the locations in the tissue section where labelling by hybridization of the conjugate has occurred.

In yet a further aspect of the invention there is provided a diagnostic kit for detecting a desired polynucleotide, which comprises an oligonucleotidepolyamide conjugate according to the present invention, wherein the oligonucleotide portion of the conjugate is complementary to a portion of the desired polynucleotide; and reagents for detecting hybridization of the conjugate.

Such a diagnostic kit may additionally comprise reagents for tissue section preparation. Examples of such reagents are formaldehyde, glutaraldehyde and acetic acid.

The present invention will now be further described with reference to the following non-limiting Examples and Figures, in which:

FIG. 1 shows a reaction scheme for solid phase peptide synthesis;

FIG. 2 shows a reaction scheme for the preparation of an oligonucleotide-polyamide conjugate;

FIG. 3 shows an Electrophoretic analysis of the crude KPIB—(AlaLys)$_5$—Ala (lane 1) and normal KPIB (lane 2) end labelled with $^{32}$P on a denaturing 20% polyacrylamide gel;

FIG. 4 shows a dot blot hybridization using biotin labelled polyamide-oligonucleotide conjugates. NC refers to negative control; and FIG. 5 shows a biotin labelled polyamide-kallikrein oligonucleotide hybridizing to a 6µm frozen section of male mouse submandibular gland. Dark areas show hybridization of the conjugate.

EXAMPLE 1

Synthesis of Reagents

4-Nitrophenyl 4-( 4,4' -dimethoxytrityloxy)butyrate (1a)- Sodium 4-hydroxybutyrate (1.26 g, 10 mmol) and 4,4'- dimethoxytrityl chloride (DMTrCl) (3.39 g, 10 mmol) were stirred in 30 mL of pyridine for 16 h. 4-nitrophenol (1.30 g, 10 mmol) and dicyclohexylcarbodiimide (DCC) (2.06 g, 10 mmol) were added and stirred for a further 2 days. The reaction mixture was filtered, and the solution was then concentrated and flash chromatographed on 70 g of silica gel with 25% EtOAc/petroleum either to give a light yellow oil (5.0 g, 95%). $^1$H NMR (CDCl$_3$) δ 2.04 (m, 2H, H$_3$), 2.7 (t, J=7.2 Hz, 2H, H$_2$), 3.2 (t, J=5.9 Hz, 2H, H$_4$), 3.77 (s, 6H, OCH$_3$), 6.8–7.5 (m, 15H, ArH) 8.2 (d, J=9.2 Hz, 2H, PhNO$_2$ m-H). $^{13}$C NMR (CDCl$_3$) δ 25.2 (C3), 31.6 (C2), 55.2 (OCH$_3$), 62.0 (C4), 86.0 (CAr$_3$), 113.1 126.8, 127.1, 127.8, 127.9,128.1, 129.1, 130.0, 136.2, 145.0, 158.4 (DMTr), 122.4, 125.1, 145.2, 155.4, (PhNO2), 171.1 (CO$_2$). The product contained some EtOAc solvent impurity.

4-Nitrophenyl 4-[ (9-phenyl-9-xanthyl)oxy]butyrate (1b). This compound was synthesized using the same method used to synthesize 1a except that pixyl chloride (PxCl) was substituted for dimethoxytrityl chloride, to give 1b in 80% yield, mp 130°–130.5° C. (EtOAc). $^1$H NMR (CDCl$_3$) δ 1.98 (m, 2H, H3), 2.7 (t, J=7.3 Hz, 2H, H2), 3.0 (t, J=5.8 Hz, 2H, H4), 7.0–7.5 (m, 15H, ArH), 8.2 (d, J=7.1 Hz, 2H PhNO$_2$ m-H). $^{13}$C NMR (CDCl$_3$) δ 25.0 (C3), 31.5 (c2), 61.s (c4), 75.4 (CPh3), 116.3, 123.2, 123.5, 126.4,126.6, 127.9, 129.1, 129.4, 148.9, 151.3 (Px C), 122.4, 125.1, 145.2, 155.4 ( PhNO$_2$ C) , 171.0 (CO$_2$).

Anal. Calcd for C$_{29}$ H$_{23}$ NO$_6$: C, 72.3; H, 4.8; N, 2.9. Found: C, 72.0; H, 4.4; N, 3.2.

4-Nitrophenyl 3-[6-(4,4'-dimethoxytrityloxy)hexylcarbamoyl]propanoate(2). A solution of succinic anhydride (1.0 g, 10 mmol) and 6-aminohexanol (1.17 gr. 10 mmol) in pyridine (10 mL) was stirred for 4 d. DMTrCl (3.39 g, 10 mmol) was then added, it was stirred for a further 4 h, and p-nitrophenol (1.39 g, 10 mmol) and DCC (2.06 g, 10 mmol) were then added and the mixture was stirred for a further 2 d. The react ion mixture was filtered, the solution concentrated and flash chromatographed on 100 g of silica gel with 50% EtOAc/petroleum either to give a light yellow oil (4.09 g, 64%). $^1$H NMR (CDCl$_3$) δ 1.2–1.7 (m, 8H, CH$_2$), 2.5 (t, J=6.5, Hz, 2H, CH$_2$), 2.93 (t, J=6.5 Hz, 2H, CH$_2$), 3.01 (t, J=6.4 Hz, 2H, CH$_2$), 3.2 (t, J=6.4 Hz, 2H, CH$_2$), 3.76 (s, 6H, OCH$_3$), 6.8–7.5 (m, 15H, ArH), 8.2 (d, J=9.2 Hz, 2H, PHNO$_2$ m-H). $^{13}$C NMR (CDCl$_3$) δ 25.83, 26.69, 29.53, 29.87, 30.55 (CH$_2$), 39.68 (CH$_2$NHCO), 55.14 (OCH$_3$), 63.16 (DMTrOCH$_2$), 85.60 (CAr$_3$), 112.91, 126.53, 127.64, 127.70, 127.79, 128.10, 129.07, 129.95, 136.60, 145.32, 158.26, (DMTr C), 122.4, 125.1, 145.31, 155.8 (PhNO$_2$ C), 170.49, 170.75 (C=0). The compound contained some EtOAc solvent impurity that could not be easily removed.

Pentafluorophenyl N-fluorenylmethoxycarbonyl-6-aminohexanoate (FmocAhaOPfp, 3). 6-Aminohexanoic acid (2.62 g, 20 mmol) and Na$_2$CO$_3$ (5.30 g, 50 mmol) were dissolved in 60 mL of H$_2$O, 25 mL of dioxan was then added, followed by N-(Fluorenylmethoxycarbonyloxy)succinimide (Fmoc-NHS) (6.75 g, 20 mmol). The mixture was stirred vigorously for 16 h. The cloudy reaction mixture was then poured into 1.2 L of H$_2$O to give a clear solution. This was extracted with EtOAc (2×300 mL) and the aqueous layer acidified to pH 3 using approximately 10 mL of conc. HCl, to give a voluminous precipitate. This was kept at 4° C. for 16 h, and was then filtered to give 6.05 g (86%) of FmocAhaOH.

To a solution of FmocAhaOH (1.77 g, 5 mmol) and pentafluorophenol (Pfp 1.01 g, 5.5 mmol) in 8 mL of DMF was added a solution of DCC (1.03 g, 5 mmol) in 2 mL of DMF. This was stirred for 16 h, filtered, and the filtrate evaporated in vacuo to dryness giving the crude ester which was recrystallized from EtOH/1% AcOH (approximately 10 mL) to give 2.41 g (93%) of white needles, mp 128°–129° C. $^1$H NMR (CDCl$_3$) δ 1.4–1.8 (m, 6H, CH$_2$), 2.7 (t, J=7.2 Hz, 2H, CH$_2$CO$_2$), 3.2 (m, 2H, NHCH$_2$), 4.2 (5, J=6.7 Mr, 1H, Fmoc CH), 4.4 (d, J=6.8 Hz, 2H, Fmoc CH$_2$), 7.3–7.8 (m, 8H, Fmoc ArH). $^{13}$C NMR (CDCl$_3$) δ 24.36 (C4), 25.93 (C3), 29.62 (C5), 33.18 (C2), 40.73 (C6), 47.31 (Fmoc CH), 66.54 (Fmoc CH$_2$), 119.98, 125.00, 127.02, 127.67 (Fmoc Aromatic CH), 141.34, 143.99 (Fmoc Aromatic C), 156.46 (Fmoc C=0), 169.36 (ester CO$_2$).

Anal. Calcd for C$_{27}$H$_{11}$NO$_4$F$_5$: C, 63.8; H, 2.2; N, 2.8. Found: C, 63.9; H, 1.8; N, 3.2.

N-(N-fluorenylmethoxycarbonyl-6-aminohexanoyl)-6-aminohexanoic acid (FmocAha$_2$OH, 6). To a solution of FmocAhaOH (prepared as above, 1.77 g, 5 mmol) and N-hydroxysuccinimide (0.575 g, 5 mmol) in 8 mL of DMF was added a solution of DCC (1.03 g, 5 mmol) in 2 Ml of DMF. It was allowed to stir for 16 h, filtered, and the filtrate evaporated in vacuo to a syrup. This was recrystallized from isopropanol (~10 mL) to give 1.94 g (86%) of 5.

To a solution of 5 (0.912 g, 2 mmol) in 10 mL dioxan was added dropwise a solution of 6-aminohexanoic acid ( 0.524 g, 4 mmol ) and Na$_2$CO$_3$ (0.424 g, 4 mmol) in 10 mL of H$_2$O. The resulting suspension was stired vigorously for 48 h, and was then poured into 100 mL of H$_2$O to give a clear solution. The pH of this rapidly stirring solution was reduced to 3 by the dropwise addition of 10 ml at 1 M KHSO$_4$. A voluminous precipitate formed, and was kept at 4° C. for 24 h, and then filtered to give a quantitative yield of the acid. This crude product was recrystallized from EtOAc to give 0.679 g (73%) of a white powder, mp 106.5°–107° C. $^1$H NMR (CD$_3$OD) δ 1.3–1.7 (m, 12H, internal CH$_2$), 2.1 (t, J=7.4 Hz, 2H, CH$_2$CONH), 2.3 (t, J=7.3 Hz, 2H, CH$_2$CO$_2$H), 3.0–3.2 (m, 4H, FmocNHCH$_2$ and CH$_2$CONHCH$_2$ ), 4.2 ( t, J=6.8 Hz, 1H, Fmoc CH), 4.3 (d, J=6.8 Hz, 2H, Fmoc CH$_2$), 7.2–7.8 (m, 8H, Fmoc ArH).

Anal. Calcd for C$_{27}$H$_{34}$N$_2$O$_5$: C, 69.5; H, 7.4; N, 6.0. Found: C, 69.2; H, 7.3; N, 5.8.

Pentafluorophenyl N-(N-Fluorenylmethoxycarbonyl-6-aminohexahoyl)-aminohexanoate (FmocAha$_2$OPfp, 4). To a solution of 6 (233 mg, 0.5 mmole) and pentafluorophenol (101 mg, 0.55 mmole) in 1 mL of DMF was added DCC (103 mg, 0.5 mmole). This was allowed to stir for 2d, and then filtered. The filtrate was evaporated in vacuo to a creamy solid which was recrystallized from 95% ETOH/1% AcOH (1 mL) to give 80 mg (57%) of pure 4, mp 126°–127° C.

Pentafluorophenyl N-tert-butoxycarbonyl-6-aminohexanoate (8). To a solution of N-Boc-6-aminohexanoic acid (4.78 g, 20.8 mmol) and pentafluorophenol (3.68 g, 20 mmol) in 50 mL of EtOAc was added DCC (4.12 g, 20 mmol). This was allowed to stir for 16 h, and was then filtered and the filtrate evaporated in vacuo to a syrup. On standing, this crystallized to give 7.46 g (94%) of the ester. Rerystallization from isopropanol/1% acetic acid gave 6.26 g of white needles, mp 81°–83° C. $^1$H NMR (CDCl$_3$) δ 1.4–1.6 (m, 15H, Boc CH$_3$ and internal CH$_2$), 1.8 (m, 2H, CH$_2$CH$_2$CO$_2$), 2.67 (5, J=7.3 Hz, 2H, CH$_2$CO$_2$), 3.1 (m, 2H, NHCH$_2$), 4.5 (b, 1H, NH). $^{13}$C NMR (CDCl$_3$) δ 24.38 (C4), 26.00 (C3), 28.39 (Boc CH$_3$), 29.70 (C5), 33.20 (C2), 40.28 (C6), 79 (Boc C), 156 (Boc C=0), 169 (Cl).

Anal. Calcd for C$_{17}$H$_{20}$NO$_4$F$_5$: C, 51.4; H, 5.1; N, 3.5. Found: C, 51.5; H, 5.0; N, 3.4.

Pentafluorophenyl N-(N-tert-butoxycarbonyl-6-aminohexanoyl)-6-aminohexanoate (BocAha$_2$OPfP, 9). To a solution of 6-aminohexanoic acid (1.31 g, 10 mmol) in 5 mL of 1 M NaOH (5 mmol) and 5 mL H$_2$O was added a solution of 8 (1.99 g, 5 mmol) in 10 mL of dioxan. The resulting fine suspension was stirred vigorously for 3 d, by which time it was clear. This solution was added to 200mL of H$_2$O, and the pH decreased to 3.5 by the dropwise addition of approximately 10 mL of 1 M KHSO$_4$, the resulting solution extracted with EtOAc (3×100 mL), dried (Na$_2$CO$_4$), and concentrated in vacuo to 3 mL. Another 10 mL of EtOAc was then added, followed by DCC (1.03 g, 5 mmol). It was stirred for 16 h, was filtered, the filtrate evaporated to dryness in vacuo, and the product was recrystallized from EtOH/H$_2$O containing 1% AcOH (approximately 10 mL), to give 1.75 g (67%) of white needles, mp 88°–89° C. $^1$H NMR (CDCl$_3$) δ 1.3–1.9 (m, 2H, CH$_2$ and Boc CH$_3$ ), 2.2 ( t, J=7.5 Hz, 2H, CH$_2$CONH), 2.7 (t, J=7.3 Hz, 2H, CH$_2$CO$_2$), 3.1 (m, 2H, Boc NHCH$_2$), 3.3 (m, 2H, CONHCH$_2$), 4.6 (bs, 1H, Boc NH), 5.6 (bs, 1H, CONH). $^{13}$C NMR (CDCl$_3$) 6 24.35, 25.31, 26.10, 26.41, 29.31, 29.83, 33.17, 36.62, 39.14, 40.35 (CH$_2$), 28.44 (Boc CH$_3$), 79.12 (Boc central C), 156.05 (Boc C=0), 169.39 (ester C=0), 172.84 (amide C=0).

Anal. Calcd for C$_{23}$H$_{31}$N$_2$O$_5$F$_5$:C, 54.1; H, 6.1; N, 5.5. Found: C, 53.9; H, 5.9; N, 5.8.

Diisobutyryl-5(and 6) -carboxyfluorescein, pentafluorophenyl ester (7). Trimellitic anhydride (9.6 g, 0.05 mol) and Resorcinol (11 g, 0.11 mol) were mixed thoroughly and placed in a 190° C. oil bath for 1 h. The temperature was then increased to 210° C., and was kept there for 5 h, by which time the melt had solidified to a dark red solid. It was then allowed to cool down and dissolved in 50 mL of DMF. To this solution was added 100 mL of pyridine and isobutyryl chloride (15.4 mL, 0.15 mol), which was allowed to stir for 24 h. Following filtration, the resulting thick syrup was redissolved in 40 mL of EtOAc, washed with 1 M H$_2$SO$_4$ (2×300 mL) and H$_2$O (1×300 mL), dried (Na$_2$SO$_4$), and again concentrated to a syrup. It was redissolved in CH$_2$Cl$_2$ and flash chromatographed on a silica gel column (170 g), eluting first with CH$_2$Cl$_2$ (800 mL) and then with 2% MeOH/CH$_2$Cl$_2$. The fractions containing the product were pooled and the solvent removed in vacuo to give 12.45 g (48%) of crude diisobutyryl-5(and 6)-carboxyfluorescein.

5.77 g of this material (11 mmol) and pentafluorophenol (2.32 g, 21.1 mmol) were dissolved in 125 mL of 1/1 EtOAc/CH$_2$Cl$_2$. The solution was cooled down to 4° C., and DCC (2.5 g, 12.1 mmol) was added dropwise. It was allowed to stir for 2 h, than filtered and the solvent removed in vacuo to give an oil, which solidified overnight at −20° C. This was redissolved in 50 mL of CH$_2$Cl$_2$ and flash chromatographed on a 150 g of silica gel, eluting with CH$_2$Cl$_2$. The fractions containing the product were pooled, the solvent removed in vacuo and the product recrystallized from 95% EtOH/2% Acetic acid, to give 3.68 g (59%) of white needles, mp 184°–188° C. On tlc (CH$_2$Cl$_2$) this gave two closely running spots, corresponding to the two isomers, at Rf 0.58 and 0.63. $^1$H NMR (CDCl$_3$) 6 1.31 (d, J=6.9 Hz, 12H, CH$_3$), 2.8 (septet, J=7.0 Hz, 2H, CH(CH$_3$)$_2$), 6.83 (s, 4H, H$_1$' and H$_2$'), 7.11 (s, 2H, H$_4$'), 7.38 (d, J=8.0 Hz, 0.5H, H$_7$ of 5-isomer), 7.96 (s, 0.5H, H$_7$ of 6-isomer), 8.20 (d, J=8.0 Hz, 0.5H, H$_6$ of 5-isomer), 8.5 (m, 1H, H$_4$ and H$_5$ of 6-isomer), 8.87 (s, 0.5H, H$_4$ of 5-isomer. $^{13}$C NMR (CDCl$_3$) 18.82, 34.18, 82.11, 82.24, 110.61, 115.07, 115.11, 118.00, 125.01, 125.89, 126.36, 127.05, 128.08, 128.71, 129.28, 130.92, 132.23, 133.30, 136.32, 137.05, 138.2, 139.62, 141.8, 142.84, 151.46, 151.51, 152.66, 53.41, 158.21, 161.06, 167.50, 174.94.

Anal. Calcd for C$_{35}$H$_{23}$F$_5$O$_9$: C, 61.6; H, 3.4. Found: C, 61.5; H, 3.0.

Since this material was analytically pure and was the material used in the fluorescein labelling experiments, it was used to determine the spectral characteristics of carboxyfluorescein (CF). A 1 μM solution of 1 in 0.1 M NH4OAc, pH 9.0 was allowed to stand for 3 d to decompose 1 to the CF nucleus, and spectral measurements taken. The extinction coefficient of this solution at 495 and 496 rum was 75000 M$^{-1}$ and at 260 nm 23000 M$^{-1}$. The extinction coefficient of the released pentafluorophenoxide ion in the same solution at 260 run is very low (170 M$^{-1}$), which is within the error limits of the absorption coefficient above, so it is not taken into account. This solution was also used as the standard reference for the fluorescence yields of fluorescein containing polyamide-oligonucleotide hybrids.

$^1$H and $^{13}$C NMR spectra were recorded on a Bruker AM300 at 300 and 75 MHz respectively with tetramethylsilane as internal reference. Dimethylformamide (DMF) was distilled under reduced pressure and used within 1–2 days. Pyridine was distilled from potassium hydroxide and stored over 5A molecular sieves. Melting points were determined in open ended capillaries on an Electrothermal Melting Point Apparatus. Flash chromatography was carried out using Merck Kieselgel # 9385.

EXAMPLE 2

Peptide Synthesis

Fmoc (Fluorenylmethoxycarbonyl) peptide synthesis methodology was used to synthesize a peptide containing multiple lysine residues that could subsequently be used as attachment sites for non-radioactive labels, and alanine residues that served as spacers between the lysine residues. This peptide has the sequence (AlaLys)$_5$Ala. Controlled Pore Glass (CPG) was used as the solid support matrix for peptide synthesis, even though this support is not common in peptide synthesis, because it is the support of choice for oligonucleotide synthesis.

The aminopropyl CPG (AP-CPG) was derivatized to generate free hydroxy groups bound to this solid support matrix, as shown in FIG. 1. To AP-CPG (Fluka, pore size 500A, 0.5 g, 20 μmol of amino groups) there was added α,ω-hydroxy carboxlic acid derivatives 1a, 1b or 2 (250μmol) and dimethylaminopyridine (DMAP) (30.5 mg, 250 μmol) in 2 ml of dimethyl formamide (DMF). This was either shaken for 3 h or left standing for 16 h. The CPG was then washed (DMF, CH$_2$Cl$_2$) and dried. The degree of functionalization is guantitated by spectrophotometric assay of dimethoxytrityl (λ=507 nm, ε=66500 M$^{-1}$) or pixyl (λ=445 nm, ε=4770 M$^{-1}$) cation released on acid treatment of a small amount of CPG. Residual amino groups (approximately 10–20%) are then acetylated by treating the CPG with acetic anhydride (Ac$_2$O) (0.5 ml, 2.5 mmol) and DMAP (50 mg, 0.4 mmol) in pyridine (2 mL) for 15 min. No significant residual amino group was detected. The CPG was then treated with 3% dichloroacetic acid in CH$_2$Cl$_2$ (2×5 min) and washed with CH$_2$Cl$_2$.

Alternatively, γ-butyrolactone was used to derivatize the CPG. In this regard, CPG (0.5 g) and γ-butyrolactone (3 ml) were placed in an oven at 60° C. for 7 days.

This modified solid support was then used for peptide synthesis. In order to couple the first amino acid (formation of an ester linkage), a high concentration of active amino acid was used. Thus, the derivatized CPG (100 mg, containing 2.7 μmol of hydroxy functionality) was reacted with a solution of N—BOC—alanine symmetrical anhydride and DMAP (0.2M in each) in DMF (2 mL) for 20 hr. Residual hydroxy groups were acetylated as before using $Ac_2O$/DMAP and the alanines deprotected to give the free amino group (25 μmol/g). The Boc group was removed from the first amino acid by treatment with 90% trifluoroacetic acid (TFA)/$H_2O$ (30 min), followed by washing ($CH_2Cl_2$), neutralization (20% triethylamine/$CH_2Cl_2$), washing ($CH_2Cl_2$) and drying. Further peptide synthesis was then carried out on a manual CRB peptide synthesizer, using standard Fmoc chemistry, by utilizing a fourfold molar excess of Fmoc-amino acid pentafluorophenyl ester and 1-hydroxybenzotriazole (HOBt) in DMF. Briefly, the CPG substrate was reacted with N—α—FMOC—N—ε—BOC—Lys pentafluorophenyl ester in DMF (2 mL) in the presence of HOBt for 30 min. The reaction was quantitative by ninhydrin assay. The FMOC group was then removed with 20% piperidine in DMF (1×3 min, 1×7 min). Subsequent couplings were carried out in the same way, alternating the lysine residues with alanines (using FMOC—Ala pentafluorophenyl ester) to synthesize $(AlaLys)_5Ala$.

EXAMPLE 3

Synthesis of an Oligonucleotide-Peptide Conjugate

The peptide synthesized according to Example 2 was used as the starting material for oligonucleotide synthesis.

The terminal amino group of the peptide was deprotected by 20% piperidine/DMF, and the CPG reacted with α,ω-hydroxycarboxylic acid linkers 1a, 1b or 2 (0.2 mmol) and 1-hydroxybenzotriazole (0.2 mM) in DFF (0.5 ml) for 16 h (see FIG. 2). Residual amino groups were acetylated and the CPG used for DNA synthesis using an Applied Biosystems 380A Automated DNA Synthesizer.

Alternatively, γ-butyrolactone was used as a linker instead of 1a, 1b or 2. In this instance, the CPG (100 mg) was reacted with 2 ml of γ-butyrolactone at 60° C. for 7 days.

The DMTr or Px protecting groups were removed from the linker group, and oligonucleotide synthesis commenced using methyl N,N-diisopropyl nucleoside phosphoramidites (Beaucage and Caruthers, Supra). Briefly, phosphoramidites are coupled as a 0.1M solution in dry acetonitrile, in the presence of 0.5M tetrazole. This is followed by acetylation of unreacted hydroxy groups ($AC_2O$/DMAP), oxidation of the phosphite triester to the phosphate ($I_2$/$H_2O$) and the detritylation (DCl/$CH_2Cl_2$) prior to coupling of the next nucleoside phosphoramidite. The first phosphoramidite was coupled onto the terminal aliphatic hydroxyl group. Oligonucleotide synthesis was continued and the 30mer oligodeoxyribonucleotide d(GGGCTTCACAACATCTGTGATGTCAGCAGG) (KPIB), complementary to part of the mRNA encoding mouse kallikrein, was synthesized on this solid support. The average coupling yield, by trityl assay, was over 99%.

In order to deprotect the conjugate, the solid support was removed from the automated synthesizer and treated with PhSH/$Et_3$N/$CH_3$CN 1:1:2 for 2 hr to remove the methyl protecting groups on the phosphotriesters. The BOC protecting groups on the lysine residues (and also the 5'-DMTr group) were removed with a 5 min treatment with 90% trifluoroacetic acid/10% ethanedithiol, followed by neutralization with 20% $Et_3$N/$CH_2Cl_2$. The ester group attaching the C-terminal amino acid to the solid support was then cleaved with conc. aq. $NH_3$ (4 hr), and the solution heated at 55° C. for a further 16 hr to remove the nucleoside amino protecting groups.

FIG. 3 shows the pattern obtained following 5'-$^{32}$P end labelling of the crude product with [γ-$^{32}$P]-ATP using polynucleotide kinase and electrophoresis on a 20% polyacrylamide gel containing 7M urea. The oligonucleotide-peptide hybrid runs slower than the normal KPIB and is the major component of the product mixture. A similar pattern is seen when the unlabelled reaction is run and the DNA visualised on the gel by UV shadowing. The pure hybrid product was obtained by preparative gel electrophoresis on a 10% gel, or by HPLC.

Amino acid analysis of the product gave the expected ratio of 6 Ala:5 Lys, with 1 mol of $(AlaLys)_5Ala$ polyamide per mole of KPIB. The product was resistant to snake venom phosphodiesterase (blocked 3'-end) and was only partially digested (10 nucleotides from the 5'-end) by spleen phosphodiesterase (as assessed by HPLC analysis of the digests). It appears that the presence of the positively charged polyamide at the 3'-end inhibits phosphodiesterase digestion in this region of the molecule. $P_1$ nuclease digested the conjugate to its component nucleoside and nucleotides.

DNA synthesis was performed with both methyl and cyanoethyl protected nucleoside phosphoramidites according to standard procedures (Beaucage and Caruthers (1981) Tetrahedron Lett., 22, pp. 1859–1862). In these synthetic procedures a 60 to 120 second capping step with DMAP/$Ac_2O$ was employed after addition of each nucleoside phosphoramidite to the support matrix.

Amino acid analyses were carried out on a Beckman System 6300 Amino Acid Analyser. Spectrofluorimetric measurements were carried out on a Perkin-Elmer LS-5 Luminescence Spectrometer. HPLC was carried out on an Altex system, using a Vydac $C_{18}$ 5 μ25 cm×4.6 nm column. Buffers used were A 0.1M triethylammonium acetate, pH 7.0 and B, 0.1M triethylammonium acetate containing 45% $CH_3$CN, at pH 7.0.

EXAMPLE 4

Synthesis of a Polyamide Containing Synthetic Amino Acids

The use of non-peptide amino acids introduces greater flexibility in the design of the molecular architecture of the polyamide. Any α,ω-aminocarboxylic acid may act as a spacer between naturally occuring amino acids. The readily available 6-aminohexanoic acid (HAhaOH) was chosen as the standard unit, but any other similar amino carboxylic acid may be used. Initially, the N-Fmoc pentafluorophenyl active ester derivatives 3 and 4 were synthesized and used successfully in the standard Fmoc peptide synthesis methodology. The dimer 4 could be prepared in good yield from the monomer 5 and 6-aminohexanoic acid. The acid 6 was also used directly in solid phase synthesis by utilizing the BOP (benzotriazol-1-yloxy-tris-(dimethylamino)-phosphonium hexafluoroborate) methodology (Castro, Supra). In the synthesis a fourfold molar excess of 6, BOP reagent, N-methylmorpholine and HOBt were used in DMF. This proved to be a very efficient way of introducing this spacer without having to make the active ester.

To illustrate the synthesis of an oligonucleotide containing a single primary aliphatic amino group well removed from the oligonucleotide part, the polyamide $Aha_4Lys(Boc)Ala$ was synthesized using the methodology described in Example 2 except that four equivalents of N-Fmoc amino acid active ester 4 was used, and utilizing two couplings of the active ester 4 to provide spacing from the oligonucleotide. A 30 met oligonucleotide complementary to part of the mouse kallikrein mRNA (KPIB) was then synthesized, after addition of the linker 2 according to the method of Example 3. The conjugate was deprotected as previously described.

In an alternative method Boc, chemistry was used for the synthesis of the polyamide. We used α-Boc-ε-FmocLysOPfp (or the corresponding carboxylic acid with BOP methodology) as the lysine derivative and BocAha$_2$OPfp as the spacer. A four fold molar excess of the active amino acid and HOBt in DMF for 0.5 h was used. The protected polyamide-oligonucleotide hybrid was deprotected in exactly the same manner as a normal oligonucleotide, to give the same product as previously described. In this case the Fmoc protecting group on the lysine residue is cleaved during the ammonia deprotection step.

The Fmoc methodology was also used to synthesize a much longer polyamide, containing ten lysine residues. This was Ala(LysAha$_4$)$_9$LysAla which was synthesized in the same manner as Aha4LysAla (Fmoc methodology) using a manual peptide synthesizer. Following the synthesis of KPIB on this substrate, the normal deprotection protocol (see Example 3) gave a product that on PAGE analysis gave a major band running slower than KPIB. PAGE purification of this band gave the product, which had a good amino acid analysis.

EXAMPLE 5

Preparation of Labelled Conjugates

Reporter groups were introduced at four different stages: (I) after polyamide synthesis; (II) after addition of the linking synthon; (III) after oligonucleotide synthesis; and (IV) after deprotection and purification of the hybrid.

(I) Biotin and fluorescein synthons were attached at this stage following removal of the Boc protecting groups on the lysine side chains. Biotin was coupled using a 0.2M solution of each of biotin, BOP reagent, HOBt and N-methylmorpholine in DMF for 30 min. This coupling can also be done during polyamide synthesis after the addition of each Lys(Boc) residue. Alternatively, biotin can be added as an active ester, such as the succinimide ester. Fluorescein was coupled at this stage by reaction with a 0.3M solution of 1 and HOBt in DMF for 3 d. Residual amino groups were acetylated. Since the subsequent piperidine treatment removes the isobutyryl protecting groups on the fluorescein, it was reacylated with DMAP/isobutyric anhydride in pyridine for 16 h.

(II) Coupling a label can be carried out at this stage if the lysine side chain protecting groups are Fmoc and Boc methodology was used for polyamide synthesis. Following removal of the ε-Fmoc group, biotin or fluorescein is added in the same manner to that in stage (I).

(III) The lysine side chain Boc protecting groups were removed as described previously (hybrid deprotection) and the label attached. Biotin is added by reacting with biotin N-hydroxysuccinimidyl active ester (20 equiv) and HOBt (20 equiv) in DMF (0.5 mL), for 16 h. Fluorescein is added as in stage (I)—but reacylation of the fluorescein is not necessary.

(IV) Biotin was added to the single lysine containing hybrid using standard methods. Fluorescein can also be added by using fluorescein isothiocyanate (FITC).

EXAMPLE 6

Fluorophore conjugation to the oligonucleotidepolyamide conjugate:

The fully protected oligonucleotide-polyamide conjugate:
CPG—SL—Ala]Lys(Boc)Aha]$_9$Lys(Boc)Ala—SL—KPIB where Aha is the 6-aminohexanoic acid residue

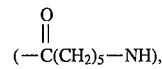

$(-C(CH_2)_5-NH)$,

SL is a linkage derived from linkers 1a or 1b, and and KPIB is the oligonucleotide whose sequence was described above, was synthesized, on 30 mg of CPG according to Example 4. The conjugate was first treated with 90% trifluoroacetic acid/10% ethanedithiol for 5 minutes, in order to remove the Lys side chain Boc protecting groups, followed by 20% triethylamine/CH$_2$Cl$_2$ to neutralize the formed primary amino groups. The conjugate was then reacted with of 40 fold excess of diisobutyrylcarboxy fluorescein pentafluorophenyl ester (107 mg) and 1-hydroxybenzotriazole (26 mg) in 0.5 ml DMF over 3 days. The resulting labelled compound was then deprotected. On polyacrylamide gel electrophoresis the labelled compound gave a strongly fluorescent band running at a similar position to the xylene cyanol dye. The band was cut out and purified to give the fluorescein labelled oligonucleotidepolyamide conjugate.

The conjugate CPG—SL—AlaLys(Boc)Aha$_4$—SL—KPIB was also synthesized according to the methods of Example 4, and labelled with fluorescein according to Example 5, stage 3. The labelled conjugate was then purified by gel electrophoresis according to methods known per se in the art.

EXAMPLE 7

Purification of Conjugates

Purification of most of the labelled and unlabelled hybrids was carried out by polyacrylamide gel electrophoresis (PAGE) using 10% gels. Purification of the single lysine containing hybrid prepared by Boc chemistry was conveniently carried out by reverse phase HPLC on a Vydac C$_{18}$ column, since the 5'-DMTr group of this hybrid is intact. The DMTr-containing hybrid was initially purified using the following conditions: isocratic at 33.3% B for 20 min, and then a gradient to 66.6% B over 30 min. DMTr—KPIB—SL—Aha$_4$LysAla elutes at 44.0 min. Detritylation of the eluate (equal volume of acetic acid, 15 min) and rechromatographing on a gradient of 0 to 66.6% B over 30 min gave the pure product, eluting at 26.0 min. The fluorescein containing hybrids may be partially purified, mainly to remove any free fluorescein and other low molecular weight material by passage through a column of Sephadex G-25 Fine (2 g) in H$_2$O. The high molecular weight fraction (0.5 mL) eluting at the void volume was collected and dialyzed exhaustively against H$_2$O.

EXAMPLE 8

Hybridization of Conjugates to Target Sequences

The following biotinylated conjugates were prepared according to the methods of Example 6.
A. KPIB—LL—Aha$_4$Lys(Biotin)Ala (labelling at stage IV)
B. KPIB—SL—[Aha$_2$Lys(Biotin)]Ala (stage II)
C. KPIB—SL—[AhaLys(Biotin)]$_{10}$Ala (stage III)

D. KPIB—SL [Aha2Lys(Biotin)]$_{10}$Ala (stage (III) LL and SL stand for the linkages derived from linkers 2 and 1 respectively. KPIB is the 30mer mouse kallikrein probe.

FIG. 4 shows the result obtained when conjugates A to D (corresponding to lanes A to D) were used to hybridize to dot blots containing a pUC plasmid with a mouse kallikrein cDNA insert. The dot blots contained a 3.7 kb plasmid derived from pUC and containing a 1 kb mouse renal kallikrein cDNA insert. The negative control (NC) was a similar pUC plasmid containing the metallothionein II$_A$ gene promoter spliced with the chloramphenicol acetyl transferase (CAT) structural gene. The nitrocellulose filters were prehybridized at 42° C. for 6.5 h in 10 mL of hybridization buffer (0.75M NaCl, 0.075M sodium citrate, 25 mM NaH$_2$PO$_4$, 25 mM Na$_2$HPO$_4$, 10 mM tetrasodium pyrophosphate, 0.1 mM disodium adenosine triphosphate, 25 mg/L salmon sperm DNA, 0.01% w/v Ficoll, 0.01% polvinylpyrrolidone, 0.01% bovine serum albumin, 20% formamide), the probe (100 ng) was then added and it was allowed to hybridize at 42° C. overnight. The filters were then washed four times, for ten minutes each, at 42° C. in 0.2×SSC (0.03M NaCl, 0.003M sodium citrate). The signal was detected using a BRL(Bethesda Research Labs) BluGENE kit, which employs a streptavidinalkaline phosphatase conjugate that binds to biotin, and a subsequent development reaction in which the enzyme acts on substrates (nitro blue tetrazolium (NBT) and 5-bromo-4-chloro-3-indoyl phosphate (BCIP) to generate an insoluble dye precipitate.

It is evident that there is no significant difference in signal between hybrids that had the biotin coupled either at stage (IV) (lane A) or stage (II) (lane B). This indicates that the conditions of oligonucleotide synthesis do not adversely effect the biotin residue so that it is not able to bind to the streptavidin conjugate. Furthermore, the hybrids containing ten biotin residues, introduced at stage (III) (lanes C and D) give a signal that is approximately ten tines stronger than that of the singly labelled hybrid. There does not appear to be a significant difference in the streptavidin binding affinity of the multiply labelled hybrid with single Aha spacers between the labels (lane C) or double Aha spacers (lane D). The relative proximity of the biotin residues therefore, does not appear to effect the ability of the streptavidin-alkaline phosphatase complex to bind to the biotin residues to a significant degree. Taking the negative control (NC) (pUC with a non-related insert) into account, the sensitivity of the singly labelled probes is 0.5 ng (220 amol) and the multi-labelled probes 0.05 ng (22 amol) by this dot blot method.

These biotinylated probes were also used to hybridize into tissue sections.

Hybridization histochemical analysis was performed according to the methods of Coghlan, J. P. et al ((1985) Anal. Biochem. 149, pp. 1–28). Briefly, 6µm frozen sections were fixed with 4% formaldehyde in 0.1M phosphate pH 7.2 for 5 min. and prehybridized for 10 min. (in 50 mM sodium phosphate pH 7.0, 5.0 mM EDTA, 0.02% ficoll, 0.02% bovine serum albumin, 0.02% polyvinyl pyrrolidone and 0.01% herring sperm DNA). Labelled conjugate was then added to a concentration of 0.8 ng/µl. Hybridization was for 3 days at 40° C. The sections (attached to glass microscope slides) were then rinsed in 4×SSC (stock solution×20 is 3M sodium chloride, 0.3M sodium citrate in distilled water). Hybridization of the conjugate was then visualised after development under a light microscope.

Probe D, containing 10 biotin residues was used to detect kallikrein mRNA in a 6 µm section of mouse submandibular gland. As shown in FIG. 5, the probe D strongly labelled (as detected by light microscopy) distinct regions of the submandibular gland, which correspond to the granular convoluted tubules, which are the site of expression of the majority of mouse kallikrein genes. Hybridization was detected using a BRL-GluGENE kit described above.

EXAMPLE 9

Synthesis of polyamide-oligonucleotide conjugates having a reactive 3'-hydroxyl group Uridine derivatives of the formula:

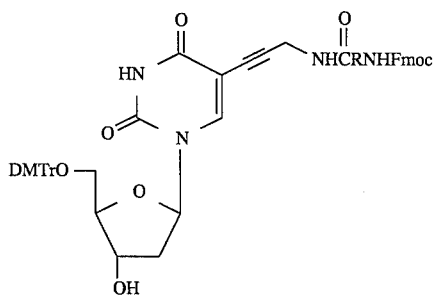

where R is alkyl or substituted alkyl, may be synthesized according to the methods of our co-pending Australian application No. PI 2666/87.

Such compounds may then be reacted with:

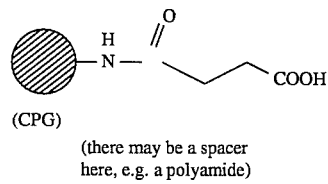

(there may be a spacer here, e.g. a polyamide)

in the presence of DCC to give:

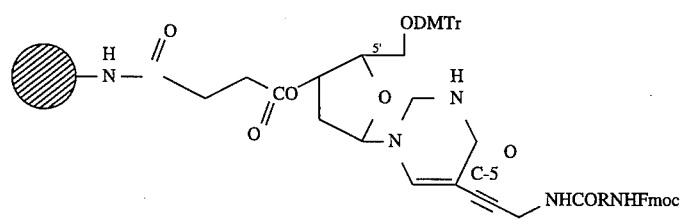

An extended polyamide can then be synthesized on the C-5 arm, and following that, the oligonucleotide synthesized on the 5'-hydroxyl group of the nucleoside.

These uridine derivatives are useful in situations where extensions to the 3'OH are required, for example in DNA sequencing. In such situations, the ester group linking the nucleoside to the CPG may be conveniently cleaved.

We claim:

1. A conjugate of the formula X—L—Y, where X is a single amino acid or a polyamide comprising two or more amino acid residues, Y is an oligonucleotide, and L is a linker that is covalently bound to the N-terminus of said single amino acid or polyamide and to the 3' phosphate group of the oligonucleotide, said linker L being derived from a) an α,ω hydroxy carboxylic acid derivative, b) a lactone, or c) a bifunctional linker having the formula R'—L'—R", wherein L' is an alkyl optionally substituted with one or more halogen, cyano, phenyl, amino, carboxy, alkyl, or alkoxy, and optionally interrupted by one or more of —S—, —O—, —NH—, —CH=CH—, —C≡C—, phenyl or —SO$_2$—, R' is a functional group that covalently binds to the N-terminus of said single amino acid or polyamide, and R" is a functional group that is the same as or different from R' and covalently binds to the 3' phosphate group of the oligonucleotide.

2. A conjugate according to claim 1, wherein X is a peptide comprised of naturally occurring amino acids.

3. A conjugate according to claim 1 or 2, wherein X contains one or more reporter groups.

4. A conjugate according to claim 3, wherein the reporter groups are selected from fluorophores, biotin, enzymes, or colloidal compounds.

5. A conjugate according to claim 4, wherein the reporter groups are selected from fluorescein, tetramethyl rhodamine, Texas Red, coumarins, carbonic anhydrase, urease, horseradish peroxidase, dehydrogenases and/or colloidal gold or silver.

6. A conjugate according to claim 1 or claim 3, wherein the polyamide is antigenic and is detectable by antibodies which bind thereto.

7. A conjugate according to claim 1 wherein said oligonucleotide is an oligodeoxyribonucleotide.

8. A conjugate according to claim 7 wherein said oligodeoxyribonucleotide is d(GGGCTTCACAACATCTGTGATGTCAGCAGG).

9. A conjugate according to claim 1 wherein L is a group of the formula:

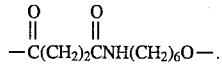

10. A conjugate according to claim 1 wherein L is derived from gamma-butyrolactone.

11. A conjugate according to claim 1 wherein L is derived from an hydroxy carboxylic acid derivative selected from the group consisting of 4-nitrophenyl 4-(4,4'-dimethoxytrityloxy)-butyrate, 4-nitrophenyl 4-[(9-phenyl-9xanthyl)oxy]-butyrate, and 4-nitrophenyl 3-[6-(4,4'-dimethoxytrityloxy)hexylcarbamoyl]propanoate.

12. A conjugate of the formula X—L—Y, where X is a polyamide comprised of amino acids, Y is an oligonucleotide comprised of deoxyribonucleotides, and L is a linker of the formula:

wherein R is C$_2$–C$_{10}$ alkyl, optionally interrupted by one or more of CO or NH.

13. A method for the production of an oligonucleotide-polyamide conjugate comprising the steps of linking the 3' terminal phosphate of a preformed oligonucleotide or nucleotide to the amino terminus of substituent X, where X is a preformed single amino acid or a polyamide comprising two or more amino acid residues, wherein said 3' terminal phosphate and said amino terminus are linked via a linker derived from a bifunctional linker having the formula R'—L'—R", wherein L' is an alkyl optionally substituted with one or more halogen, cyano, phenyl, amino, carboxy, alkyl, or alkoxy, and optionally interrupted by one or more of —S—, —O—, —NH—, —CH=CH—, —C≡C—, phenyl or —SO$_2$—, R' is a functional group that covalently binds to the N-terminus of said single amino acid or polyamide, and R" is a functional group that is the same as or different from R' and covalently binds to the 3' phosphate group of the oligonucleotide.

14. A method for the synthesis of a conjugate as claimed in claims 1–6, the said method comprising the steps of:

(a) reacting the C-terminus of a first amino acid or a unit of amino acids (linked together by amide bonds) with a support matrix to form a bond therebetween;

(b) thereafter sequentially reacting the support matrix with one or more amino acids, according to well-known solid-phase peptide synthetic techniques to form a polyamide;

(c) reacting the support matrix-polyamide with a first reactive group of a linker to form a bond between the amino terminus of the polyamide and the linker;

(d) reacting the product of step (c) with a first nucleotide to form a bond between a second reactive group on the linker and the 3' phosphate of the nucleotide;

(e) thereafter sequentially reacting the support matrix with one or more nucleotides, according to well-known solid phase oligonucleotide synthetic methods to form an oligonucleotide; and (f) optionally cleaving the conjugate from the support matrix and removing any protecting groups associated with reactive groups of the polyamide or oligonucleotide, and purifying the resulting conjugate.

15. A method for determining the presence and location in animal or plant tissue of a target polynucleotide which comprises:

(a) preparing a section of the tissue to be examined;

(b) hybridizing the tissue section with a conjugate according to any one of claim 1, 2, 3, 4, 5 or 6, wherein the oligonucleotide portion of the conjugate is complementary to a portion of said target polynucleotide;

(c) removing unhybridized probe material from the tissue section; and (d) detecting or identifying the locations in the tissue section where labelling by hybridization of the conjugate has occurred as an indication of the presence and location in said animal or plant tissue of said target polynucleotide.

16. A method for detecting a target polynucleotide immobilized to or otherwise associated with a support matrix, said method comprising contacting the support matrix with a conjugate according to any one of claim 1, 2, 4, 5, or 6 wherein the oligonucleotide portion of the conjugate is complementary to a portion of the target polynucleotide, and thereafter detecting whether hybridization of the conjugate has occurred as an indication of the presence of said target polynucleotide.

17. A method for detecting the presence or absence of a specific viral, bacterial or other target polynucleotide in a biological sample, comprising contacting the nucleic acids of the sample with a conjugate according to any one of claim 1, 2, 4, 5, or 6 wherein the oligonucleotide portion of the conjugate is complementary to a portion of said target polynucleotide, and thereafter detecting whether hybridization of the conjugate has occurred as an indication of the presence of said target polynucleotide in said biological sample.

18. A diagnostic kit for detecting a desired polynucleotide, which comprises a conjugate according to claims 1–6, wherein the oligonucleotide portion of the conjugate is complementary to a portion of the desired polynucleotide; and reagents for detecting hybridization of the conjugate.

19. A diagnostic kit according to claim 18 for use in determination of the presence and location in animal or plant tissue of a specific polynucleotide population, which additionally comprises reagents for tissue section preparation.

* * * * *

UNITED STATES PATENT AND TRADEMARK OFFICE
CERTIFICATE OF CORRECTION

PATENT NO. : 5,525,465

DATED : June 11, 1996

INVENTOR(S) : HARALAMBIDIS et al.

It is certified that error appears in the above-indentified patent and that said Letters Patent is hereby corrected as shown below:

Column 2, line 61, delete "Fluoro phore" and insert therefor --Fluorophore--.

Column 2, line 62, delete "fluore scein" and insert therefor --fluorescein--.

Column 3, line 7, delete "-(CP)," and insert therefor --(CP),--.

Column 4, line 6, delete "OR" and insert therefor ---OR--.

Column 4, line 18, delete "C=C" and insert therefor --C≡C--.

Column 4, line 24, delete "L" and insert therefor --L'--.

Column 5, line 26, delete "J. Them" and insert therefor --J. Chem.--.

Column 6, line 52, delete "Goldlath" and insert therefor --Goldfarb--.

Column 6, line 61, delete "of vital" and insert therefor --of viral--.

Column 7, line 4, delete "of vital" and insert therefor --of viral--.

Column 7, line 49, delete "of vital" and insert therefor --of viral--.

Column 9, lines 23-24, delete "(c2), 61.s (c4)" and insert therefor --(C2), 61.9 (C4)--.

UNITED STATES PATENT AND TRADEMARK OFFICE
CERTIFICATE OF CORRECTION

PATENT NO. : 5,525,465

DATED : June 11, 1996

INVENTOR(S) : HARALAMBIDIS et al.

It is certified that error appears in the above-indentified patent and that said Letters Patent is hereby corrected as shown below:

Column 9, line 36, delete "reac tion" and insert therefor --reaction--.

Column 10, line 2, delete "from EtOH/%" and insert therefor --from 95% EtOH/%--.

Column 10, line 48, delete "give 80 mg" and insert therefor --give 180 mg--.

Column 10, line 57, delete "Rerystallization" and insert therefor --Recrystallization--.

Column 11, line 17, delete "6 24.35" and insert therefor --δ 24.35--.

Column 11, line 55, delete "6 1.31" and insert therefor --δ 1.31--.

Column 11, line 64, delete "53.41" and inser therefor --153.41--.

Column 12, line 4, delete "1 in 0.1 M NH4OAc," and insert therefor --$\underline{7}$ in 0.1 M NM$^4$OAc--.

Column 12, line 7, delete "496 run" and insert therefor --496 nm--.

Column 12, line 10, delete "260 run" and insert therefor --260 nm--.

Column 12, line 44, delete "carboxlic" and insert therefor --carboxylic--.

UNITED STATES PATENT AND TRADEMARK OFFICE
CERTIFICATE OF CORRECTION

PATENT NO. : 5,525,465

DATED : June 11, 1996

INVENTOR(S) : HARALAMBIDIS et al.

It is certified that error appears in the above-indentified patent and that said Letters Patent is hereby corrected as shown below:

Column 12, line 48, delete "guantitated" and insert therefor --quantitated--.

Column 13, line 67, delete "30 met" and insert therefor --30 mer--.

Column 15, line 48, delete "of 1 and" and insert therefor --of 7 and--.

Column 16, line 12, delete "and and KPIB" and insert therefor --and KPIB--.

Column 17, line 36 delete "ten tines" and insert therefor --ten times--.

Column 19, claim 1, line 11, delete "C=C" and insert therefor --C≡C--.

Column 19, claim 11, line 45, delete "an hydroxy" and insert therefor --αω hydroxy--.

Column 20, claim 13, line 5, delete "C=C" and insert therefor --C≡C--.

Signed and Sealed this

Twenty-second Day of July, 1997

Attest:

BRUCE LEHMAN

Attesting Officer

Commissioner of Patents and Trademarks